(12) United States Patent
Yu et al.

(10) Patent No.: US 12,274,280 B2
(45) Date of Patent: Apr. 15, 2025

(54) METHOD FOR EXTRACTING OILS FROM SAUCES WHILE SIMULTANEOUSLY DETERMINING FAT CONTENT, PEROXIDE VALUE, AND ACID VALUE

(71) Applicant: HENAN ZHONGDA HENGYUAN BIOTECHNOLOGY STOCK CO., LTD., Luohe (CN)

(72) Inventors: Chunfeng Yu, Luohe (CN); Ziheng Jin, Luohe (CN); Yanjun Wen, Luohe (CN); Linzheng Li, Luohe (CN); Tiantian Wang, Luohe (CN); Honglong Li, Luohe (CN); Wenjin Zhang, Luohe (CN); Haitao Han, Luohe (CN); Congcong Zhao, Luohe (CN); Di Wang, Luohe (CN)

(73) Assignee: HENAN ZHONGDA HENGYUAN BIOTECHNOLOGY STOCK CO., LTD., Luohe (CN)

( * ) Notice: Subject to any disclaimer, the term of this patent is extended or adjusted under 35 U.S.C. 154(b) by 0 days.

(21) Appl. No.: 18/899,337

(22) Filed: Sep. 27, 2024

(65) Prior Publication Data
US 2025/0017247 A1   Jan. 16, 2025

(51) Int. Cl.
*A23L 27/60*   (2016.01)
*B01D 11/04*   (2006.01)
(Continued)

(52) U.S. Cl.
CPC .......... *A23L 27/60* (2016.08); *B01D 11/0492* (2013.01); *C11B 3/006* (2013.01);
(Continued)

(58) Field of Classification Search
CPC .......... A23L 27/60; C11B 3/006; C11B 1/10; G01N 5/00; G01N 1/30; G01N 1/38;
(Continued)

(56) References Cited

U.S. PATENT DOCUMENTS 4,554,132 A * 11/1985 Collins .................... G01N 5/04
                                                              422/74
2009/0075325 A1 * 3/2009 Das ........................ G01N 24/08
                                                              250/311

(Continued)

FOREIGN PATENT DOCUMENTS

CA      2749963 A1 *  8/2010   .......... A23L 3/3472
CN      102519957 A    6/2012
(Continued)

OTHER PUBLICATIONS

Mouyong Zou et al, "Changes in lipids distribution and fatty acid composition during soy sauce production", published by Food Science and Nutrition, 2019, vol. 7, pp. 764-772. (Year: 2019).*

(Continued)

*Primary Examiner* — Joseph W Drodge

(57) ABSTRACT

A method for extracting oils from sauces while simultaneously determining fat content, peroxide value, and acid value is disclosed. The method is simple to operate and requires uncomplicated equipment. It features a short testing cycle and high efficiency, and suitable for the extraction of oils from oil-rich emulsified encapsulated sauces (such as salad dressings) with high extraction rates. The determination of peroxide value and acid value is not affected by (Continued)

pretreatment methods, ensuring more representative results. It addresses the challenges of difficult oil separation and extraction from oil-rich emulsified encapsulated sauces and solves significant issues encountered when using acid hydrolysis and alkaline hydrolysis methods to determine peroxide value and acid value. It enables the simultaneous monitoring of three physicochemical indicators (fat content, peroxide value, and acid value). This high-efficiency method is particularly suitable for tracking and monitoring during the production process, thereby enhancing production efficiency and reducing production costs.

5 Claims, 1 Drawing Sheet

(51) Int. Cl.
 C11B 3/00 (2006.01)
 G01N 1/40 (2006.01)
 G01N 33/03 (2006.01)
(52) U.S. Cl.
 CPC ........... *G01N 1/4055* (2013.01); *G01N 33/03* (2013.01); *Y10T 436/255* (2015.01)
(58) Field of Classification Search
 CPC ...... G01N 1/4055; G01N 1/4077; G01N 1/44; G01N 33/02; G01N 2001/4061; G01N 1/40; G01N 2001/4088; G01N 5/04; G01N 33/03; B01D 3/42; B01D 5/0057; B01D 5/0072; B01D 11/04; B01D 11/0488; B01D 11/0492; B01D 36/00; Y10T 436/25125; Y10T 436/25375; Y10T 436/255
See application file for complete search history.

(56) References Cited

U.S. PATENT DOCUMENTS

| 2014/0096598 | A1* | 4/2014 | Halverson | G01N 15/04 73/61.72 |
|---|---|---|---|---|
| 2017/0010199 | A1* | 1/2017 | Halverson | G01N 15/042 |
| 2019/0303374 | A1* | 10/2019 | Doble | G06F 16/248 |
| 2021/0123897 | A1* | 4/2021 | Liu | B01D 11/0492 |

FOREIGN PATENT DOCUMENTS

| CN | 105572115 A | 5/2016 | | |
|---|---|---|---|---|
| CN | 105950285 A | 9/2016 | | |
| CN | 106908567 B | 10/2019 | | |
| CN | 111650014 A | 9/2020 | | |
| WO | WO-2015147403 A1 * | 10/2015 | | G01N 21/25 |
| WO | WO-2017093867 A1 * | 6/2017 | | G01N 33/06 |

OTHER PUBLICATIONS

Rina Rifqie Mariana et al, Analysis of peroxide value, free fatty acid, and water content changes in used cooking oil from street vendors in Malang, presented in AIP Conference, 2231, 040057, published 2020. (Year: 2020).*

Dr. Shashikant Pardeshi, "Determination of Oxidative Status of Different Brands of Rice Bran Cooking Oils Before and After Frying Available in Market", published in International Journal for Innovative Research in Science and Technology, vol. 7, Issue 4, Sep. 2020. (Year: 2020).*

Rabeea M. Mahmood et al, "Effects of Soy Sauce and Some Other Additives on Lipid Oxidation and Its Related Properties of Minced Beef Meat during Cold Storage", presented in Fourth International Conference for Agricultural and Sustainability Sciences, IOP Conference Series: 910, 2021. (Year: 2021).*

* cited by examiner

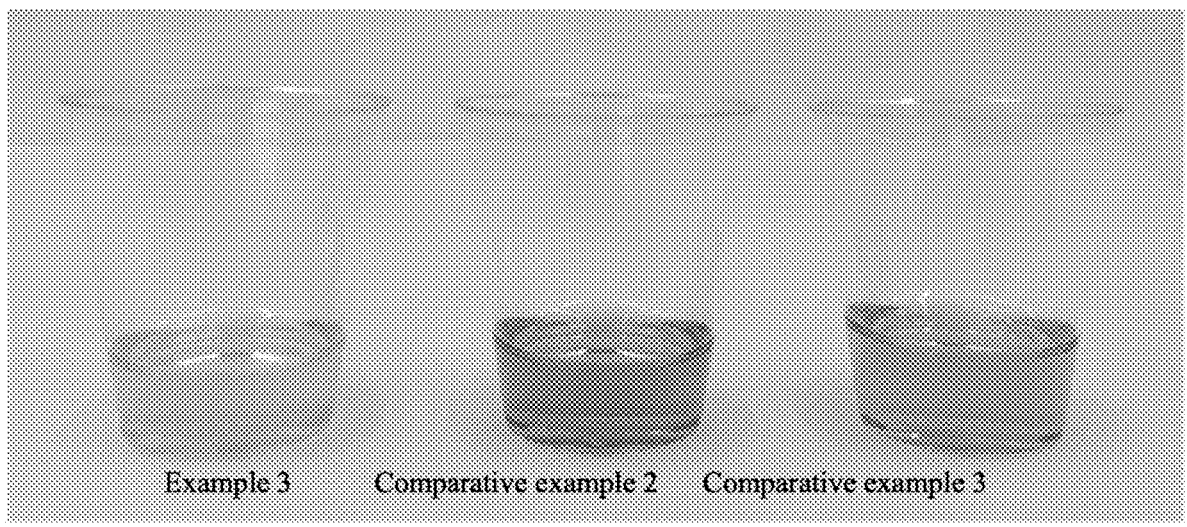

METHOD FOR EXTRACTING OILS FROM SAUCES WHILE SIMULTANEOUSLY DETERMINING FAT CONTENT, PEROXIDE VALUE, AND ACID VALUE

This application claims priority to Chinese Patent Application No. 202310938319.8, filed on Jul. 27, 2023, which is incorporated by reference for all purposes as if fully set forth herein.

TECHNICAL FIELD

The invention relates to the field of food technology, particularly to a method for extracting oils from sauces while simultaneously determining fat content, peroxide value, and acid value.

BACKGROUND

China has a long history of dietary culture, and with the development of society, the variety of dishes has become increasingly rich, and the ways of eating have become more diverse. The condiment industry related to food has also experienced rapid growth, and a wide range of sauce products have emerged. In recent years, with the development of convenience foods and the rapid increase in the variety of condiments, people's demands for product quality and safety have become more pronounced. Some types of sauces are rich in oil, and the stability of the oil content in their formulations is essential to ensure product quality. At the same time, the peroxide value and acid value of the oil have become key control points for evaluating product quality and safety.

Currently, the market offers oil-rich emulsified encapsulated sauces (such as salad dressing ingredients: water, soybean oil, sugar, vinegar, egg yolk liquid (containing proteins, phospholipids, etc.), acid-treated starch, hydroxypropyl distarch phosphate, xanthan gum, citric acid, salt, spices, etc.), with oil content reaching as high as 30-50%. Raw materials with emulsifying and thickening properties create a stable system where the oil is emulsified and encapsulated within the product, ensuring stability for up to 9 months. While the stable emulsified encapsulated system guarantees product quality, it poses significant challenges for subsequent validation, monitoring, and testing. Current detection methods are insufficient to meet the testing requirements and cannot efficiently and effectively monitor and verify the production process.

Furthermore, research on methods for extracting oils and determining peroxide value and acid value has primarily focused on products like milk powder and non-dairy creamers. However, there is limited information on extraction rate validation for monitoring oil content during the production process, and even fewer methods that can simultaneously meet the requirements for extraction rate, peroxide value, and acid value. For example, CN105950285A disclosed a method for extracting fat from dairy products and determining the peroxide value of the fat. The fat is obtained by mixing dairy products with ethanol, water, and petroleum ether, standing for 12 hours, filtering, and performing rotary evaporation. CN105572115A described a method for extracting fat from non-dairy creamer and determining its peroxide value, which involves mixing non-dairy creamer with water and hydrochloric acid, performing acid hydrolysis at a temperature of 70-80° C. for 1 hour, then mixing the obtained acid hydrolysis product with ethanol and ether, standing for at least 12 hours, and evaporating the ether layer to obtain the fat. CN102519957A disclosed a method for detecting the peroxide value in milk powder using water, ethanol, and ether to extract the oil. CN106908567B disclosed a method for determining the peroxide value of fat in infant formula, which involves magnetic stirring, ultrasonication, and centrifugation to collect the upper organic phase, followed by rotary evaporation to obtain the fat. CN111650014A disclosed a method for extracting sample oil to determine the peroxide value and acid value in fatty foods, which involves soaking granular samples in petroleum ether for extraction, followed by filtration and solvent evaporation to obtain the oil. There is almost no research related to oil-rich emulsified encapsulated sauces (such as salad dressings).

SUMMARY OF THE INVENTION

To address the deficiencies and limitations in the prior art, the primary objective of the present invention is to provide a method for extracting oil from sauces while simultaneously determining fat content, peroxide value, and acid value. This method is applicable to the extraction of oil and the determination of fat content, peroxide value, and acid value in oil-rich emulsified encapsulated sauces (such as salad dressings). The method involves diluting the sauce with water to reduce its viscosity, using sodium chloride to alter the charge balance of the emulsified sauce system, adding ethanol to reduce the emulsifying encapsulation properties of additives such as emulsifiers, proteins, and thickeners, and performing stepwise extraction with petroleum ether. Anhydrous sodium sulfate is used for dehydration, and the oil is prepared using rotary evaporation under vacuum and nitrogen blowing. This method allows for the determination of fat content (to monitor the stability of the product formulation), peroxide value, and acid value (to monitor the quality stability of the product). The entire process is simple to operate, requires minimal equipment, has a short testing cycle, and is highly efficient, making it particularly suitable for continuous monitoring during industrial production.

In order to achieve the above object, the present invention provides a method for extracting oil from sauces and simultaneously determining fat content, peroxide value, and acid value, comprising the following steps:

(1) adding water in an amount that is 0.5 to 3 times the weight of the sauces to the sauces, stirring at 500 to 2000 rpm for 2 to 5 minutes to disperse uniformly and obtain a suspension, wherein the sauces are oil-rich emulsified encapsulated sauces;

(2) under stirring conditions of 500 to 1000 rpm, adding edible salt amounting to 2-5% of the mass of the suspension and stirring until completely dissolved;

(3) adding 95% ethanol (by volume) in an amount that is 1 to 3 times the weight of the sauces, stirring at 500 to 1000 rpm for 2 to 5 minutes to mix and disperse evenly;

first extraction: adding petroleum ether in an amount that is 1 to 3 times the weight of the sauces, stirring at 500 to 1000 rpm for 2 to 5 minutes to mix and disperse uniformly, and letting it stand for 10 to 15 minutes to form three distinct layers from top to bottom: a petroleum ether oil phase layer, an emulsified sauce layer, and an aqueous phase layer. Using a pipette to extract the upper petroleum ether oil phase layer, leaving the emulsified sauce layer and aqueous phase layer mixture;

second extraction: adding petroleum ether in an amount that is 1 to 1.5 times the weight of the sauces to the emulsified sauce layer and aqueous phase layer remaining from the first extraction, stirring at 300 to 700 rpm for 2 to 5 minutes to mix and disperse uniformly, and letting it stand for 5 to 10 minutes to form three distinct layers from top to bottom: a petroleum ether oil phase layer, an emulsified sauce layer, and an aqueous phase layer. Using a pipette to extract the upper petroleum ether oil phase layer, leaving the emulsified sauce layer and aqueous phase layer mixture;

third extraction: adding petroleum ether in an amount that is 0.5 to 1.0 times the weight of the sauces to the emulsified sauce layer and aqueous phase layer remaining from the second extraction, stirring at 300 to 700 rpm for 2 to 5 minutes to mix and disperse uniformly, and letting it stand for 5 to 10 minutes to form three distinct layers from top to bottom: a petroleum ether oil phase layer, an emulsified sauce layer, and an aqueous phase layer. Using a pipette to extract the upper petroleum ether oil phase layer. Combining the petroleum ether oil phase layers obtained from the first, second, and third extractions to obtain petroleum ether oil mixture;

(5) filtering the petroleum ether oil mixture obtained in step (4) through an anhydrous sodium sulfate funnel, collecting it into a recovery bottle of constant weight, then rinsing the filter paper and funnel with 5-20 mL of blank petroleum ether, and collecting the dehydrated petroleum ether oil mixture;

(6) performing rotary evaporation on the dehydrated petroleum ether oil mixture obtained in step (5) at a temperature of 25-40° C. and a vacuum degree of −0.04 to −0.09 MPa, using a condenser at −5 to −20° C. to recover the petroleum ether until no petroleum ether drips from the condenser and the oil has no petroleum ether odor. Continue rotary evaporation for an additional 5-10 minutes to further reduce solvent residue, obtaining the oil in the recovery bottle;

(7) wiping the surface of the recovery bottle multiple times, then blowing with nitrogen gas at a pressure of 0.01-0.2 MPa for 5-30 minutes to further reduce solvent residue in the oil, and reducing the oil to room temperature under nitrogen protection to minimize the effects of high-temperature oxidation;

(8) testing the fat content, peroxide value, and acid value of the oil after nitrogen blowing in step (7);

The petroleum ether used in steps (4) and (5) has a boiling range of 30-60° C.

The fat content test in step (7) is conducted according to the following formulas:

fat content=(mass of extracted oil/mass of sauce sample)×100%;

oil extraction rate=[(mass of recovery bottle with extracted oil−mass of recovery bottle)/added oil amount]×100%. (where the added oil amount=mass of sauce sample×theoretical oil content of the sauce).

The peroxide value in step (7) is tested according to the sample determination method in GB 5009.227-2016; The acid value is tested according to the sample determination method in GB 5009.229-2016.

The oil-rich emulsified encapsulated sauce in step (1) is salad dressing, and the water is RO water; the edible salt in step (2) is non-iodized salt or NaCl.

The anhydrous sodium sulfate funnel in step (5) contains anhydrous sodium sulfate in an amount that is 10-30% of the theoretical oil content in the sauce.

In step (7), the recovery bottle is wiped multiple times by first using dry gauze to remove moisture from the surface, then using gauze soaked in anhydrous ethanol to wipe the surface, and finally using dry gauze to remove any residual ethanol from the surface.

Principle of the Invention

The invention reduces the viscosity of thickeners, emulsifiers, proteins, and other additives in the sauce by diluting the sauce with water.

The invention reduces the emulsifying encapsulation properties of the emulsified sauce system by adding sodium chloride to alter its charge balance.

The invention further disrupts the emulsification balance by adding ethanol, thereby reducing the embedding performance of auxiliary materials such as emulsifiers, proteins, and thickeners.

The invention ensures the extraction rate of oil and meets the requirements for fat content testing by using petroleum ether as a single solvent for stepwise extraction.

The invention removes trace amounts of water and reduces interference with subsequent tests by using anhydrous sodium sulfate for filtration and dehydration.

The invention removes a single organic solvent (which can be reused) by vacuum rotary evaporation, thereby reducing the impact of oxygen, high temperatures, and prolonged exposure on the oil;

The invention involves wiping the recovery bottle with anhydrous ethanol followed by nitrogen blowing. This process not only reduces solvent residue in the oil in one step but also lowers the temperature of the extracted oil to room temperature under nitrogen protection, thereby reducing the impact of high-temperature oxidation, ensuring that the prepared samples for fat content, peroxide value, and acid value tests are more representative.

The present invention offers the following advantages and effects compared to the prior art:

The present invention is simple to operate and requires uncomplicated equipment. It features a short testing cycle and high efficiency. It is suitable for the extraction of oils from oil-rich emulsified encapsulated sauces (such as salad dressings) with high extraction rates. The determination of peroxide value and acid value is not affected by pretreatment methods, ensuring more representative results. This invention addresses the challenges of difficult oil separation and extraction from oil-rich emulsified encapsulated sauces and solves the significant issues encountered when using acid hydrolysis and alkaline hydrolysis methods to determine peroxide value and acid value. It enables the simultaneous monitoring of three physicochemical indicators (fat content, peroxide value, and acid value). This high-efficiency method is particularly suitable for tracking and monitoring during the production process.

DESCRIPTION OF THE DRAWING

FIG. 1 is a photo showing the color differences between oils extracted using different methods.

DETAILED DESCRIPTION OF EMBODIMENTS

The following specific embodiments further illustrate the content of the present invention and should not be construed as limiting the scope of the invention.

Example 1

(1) Adding 160 g of RO water to 80.35 g of salad dressing (with a theoretical oil content of 40% by weight), stirring at 1000 rpm for 3 minutes to disperse uniformly and obtain a suspension. Under stirring conditions of 1000 rpm, slowly adding edible salt amounting to 3% of the mass of the suspension and stirring until completely dissolved. Then, slowly adding 95% ethanol (by volume) in an amount that is 2 times the weight of the salad dressing, stirring at 1000 rpm for 3 minutes to mix and disperse evenly;

(2) First extraction: slowly adding petroleum ether (boiling range 30-60° C.) in an amount that is 2 times the weight of the salad dressing, stirring at 1000 rpm for 3 minutes to mix and disperse uniformly, and letting it stand for 15 minutes to form three distinct layers from top to bottom: a petroleum ether oil phase layer, an emulsified sauce layer, and an aqueous phase layer. Using a pipette to extract the upper petroleum ether oil phase layer, leaving the emulsified sauce layer and aqueous phase layer mixture;

second extraction: adding petroleum ether (boiling range 30-60° C.) in an amount that is equal to the weight of the remaining emulsified sauce layer and aqueous phase layer from the first extraction, stirring at 500 rpm for 3 minutes to mix and disperse uniformly, and letting it stand for 10 minutes to form three distinct layers from top to bottom: a petroleum ether oil phase layer, an emulsified sauce layer, and an aqueous phase layer. Using a pipette to extract the upper petroleum ether oil phase layer, leaving the emulsified sauce layer and aqueous phase layer mixture;

third extraction: adding petroleum ether (boiling range 30-60° C.) in an amount that is 0.5 times the weight of the remaining emulsified sauce layer and aqueous phase layer from the second extraction, stirring at 500 rpm for 3 minutes to mix and disperse uniformly, and letting it stand for 10 minutes to form three distinct layers from top to bottom: a petroleum ether oil phase layer, an emulsified sauce layer, and an aqueous phase layer. Using a pipette to extract the upper petroleum ether oil phase layer. Combining the petroleum ether oil phase layers obtained from the first, second, and third extractions to obtain a petroleum ether oil mixture.

(3) Filtering the petroleum ether oil mixture obtained in step (2) through an anhydrous sodium sulfate funnel (with anhydrous sodium sulfate in an amount equal to 20% of the theoretical mass of oil in the sauce), collecting it into a recovery bottle of constant weight (118.14 g), then rinsing the filter paper and funnel with 15 mL of blank petroleum ether, and collecting the dehydrated petroleum ether oil mixture;

(4) Performing rotary evaporation on the dehydrated petroleum ether oil mixture obtained in step (3) at a temperature of 35° C. and a vacuum degree of −0.09 MPa, using a condenser at −12° C. to recover the petroleum ether until no petroleum ether drips from the condenser and the oil has no petroleum ether odor. Continue rotary evaporation for an additional 8 minutes to further reduce solvent residue, obtaining the oil in the recovery bottle;

(5) Wiping the surface of the recovery bottle multiple times (first using dry gauze to remove moisture from the surface of the recovery bottle, then using gauze soaked in anhydrous ethanol to wipe the surface, and finally using dry gauze to remove any residual ethanol from the surface of the recovery bottle). Blowing with nitrogen gas at a pressure of 0.1 MPa for 20 minutes to further reduce solvent residue in the oil, and reducing the oil to room temperature under nitrogen protection to minimize the effects of high-temperature oxidation. After cooling, weighing the recovery bottle containing the oil, which is 148.85 g;

(6) Testing the fat content, peroxide value, and acid value of the oil after nitrogen blowing in step (5). The fat content is tested as follows:

fat content=(148.85−118.14)/80.35×100%=38.22%
[oil extraction rate=(148.85−118.14)/(80.35× 0.4)×100%=95.55%], the oil is transparent light yellow;

the peroxide value is tested to be 0.046 g/100 g, according to the method specified in GB 5009.227-2016;

the acid value is tested to be 0.52 mg/g, according to the method specified in GB 5009.229-2016.

Example 2

(1) Adding 160 g of RO water to 80.40 g of salad dressing (with a theoretical oil content of 40% by weight), stirring at 1000 rpm for 3 minutes to disperse uniformly and obtain a suspension. Under stirring conditions of 1000 rpm, slowly adding edible salt amounting to 5% of the mass of the suspension and stirring until completely dissolved. Then, slowly adding 95% ethanol (by volume) in an amount that is 2 times the weight of the salad dressing, stirring at 1000 rpm for 3 minutes to mix and disperse evenly;

(2) First extraction: slowly adding petroleum ether (boiling range 30-60° C.) in an amount that is 2.5 times the weight of the salad dressing, stirring at 1000 rpm for 3 minutes to mix and disperse uniformly, and letting it stand for 15 minutes to form three distinct layers from top to bottom: a petroleum ether oil phase, an emulsified sauce layer, and an aqueous phase. Using a pipette to extract the upper petroleum ether oil phase, leaving the emulsified sauce layer and aqueous phase layer mixture;

second extraction: adding petroleum ether (boiling range 30-60° C.) in an amount that is equal to the weight of the remaining emulsified sauce layer and aqueous phase layer from the first extraction, stirring at 500 rpm for 3 minutes to mix and disperse uniformly, and letting it stand for 10 minutes to form three distinct layers from top to bottom: a petroleum ether oil phase, an emulsified sauce layer, and an aqueous phase. Using a pipette to extract the upper petroleum ether oil phase, leaving the emulsified sauce layer and aqueous phase layer mixture;

third extraction: adding petroleum ether (boiling range 30-60° C.) in an amount that is equal to the weight of the remaining emulsified sauce layer and aqueous phase layer from the second extraction, stirring at 500 rpm for 3 minutes to mix and disperse uniformly, and letting it stand for 10 minutes to form three distinct layers from top to bottom: a petroleum ether oil phase, an emulsified sauce layer, and an aqueous phase. Using a pipette to extract the upper petroleum ether oil phase. Combining the petroleum ether oil phases obtained from the first, second, and third extractions to obtain a petroleum ether oil mixture;

(3) Filtering the petroleum ether oil mixture obtained in step (2) through an anhydrous sodium sulfate funnel (with anhydrous sodium sulfate in an amount equal to 20% of the theoretical mass of oil in the sauce), collecting it into a recovery bottle of constant weight (112.12 g), then rinsing the filter paper and funnel with 15 mL of blank petroleum ether, and collecting the dehydrated petroleum ether oil mixture;

(4) Performing rotary evaporation on the dehydrated petroleum ether oil mixture obtained in step (3) at a temperature of 35° C. and a vacuum degree of −0.09 MPa, using a condenser at −12° C. to recover the petroleum ether until no petroleum ether drips from the condenser and the oil has no petroleum ether odor. Continue rotary evaporation for an additional 8 minutes to further reduce solvent residue, obtaining the oil in the recovery bottle;

(5) Wiping the surface of the recovery bottle multiple times (first using dry gauze to remove moisture from the surface of the recovery bottle, then using gauze soaked in anhydrous ethanol to wipe the surface, and finally using dry gauze to remove any residual ethanol from the surface of the recovery bottle). Blowing with nitrogen gas at a pressure of 0.1 MPa for 20 minutes to further reduce solvent residue in the oil, and reducing the oil to room temperature under nitrogen protection to minimize the effects of high-temperature oxidation. After cooling, weighing the recovery bottle containing the oil, which is 143.15 g;

(6) Testing the fat content, peroxide value, and acid value of the oil after nitrogen blowing in step (5). The fat content is tested as follows:

fat content=(143.15−112.12)/80.40×100%=38.59% [oil extraction rate=(143.15−112.12)/(80.40× 0.4)×100%=96.49%], the oil is transparent light yellow;

the peroxide value is tested to be 0.053 g/100 g, according to the method specified in GB 5009.227-2016;

the acid value is tested to be 0.49 mg/g, according to the method specified in GB 5009.229-2016.

Example 3

(1) Adding 100 g of RO water to 100.18 g of composite sauce (with a theoretical oil content of 30% by weight), stirring at 1000 rpm for 3 minutes to disperse uniformly and obtain a suspension. Under stirring conditions of 1000 rpm, slowly adding edible salt amounting to 4% of the mass of the suspension and stirring until completely dissolved. Then, slowly adding 95% ethanol (by volume) in an amount that is 2.5 times the weight of the sauce, stirring at 1000 rpm for 3 minutes to mix and disperse evenly;

(2) First extraction: slowly adding petroleum ether (boiling range 30-60° C.) in an amount that is 2.5 times the weight of the sauce, stirring at 1000 rpm for 3 minutes to mix and disperse uniformly, and letting it stand for 15 minutes to form three distinct layers from top to bottom: a petroleum ether oil phase, an emulsified sauce layer, and an aqueous phase. Using a pipette to extract the upper petroleum ether oil phase, leaving the emulsified sauce layer and aqueous phase layer mixture;

second extraction: adding petroleum ether (boiling range 30-60° C.) in an amount that is equal to the weight of the remaining emulsified sauce layer and aqueous phase layer from the first extraction, stirring at 500 rpm for 3 minutes to mix and disperse uniformly, and letting it stand for 10 minutes to form three distinct layers from top to bottom: a petroleum ether oil phase, an emulsified sauce layer, and an aqueous phase. Using a pipette to extract the upper petroleum ether oil phase, leaving the emulsified sauce layer and aqueous phase layer mixture;

third extraction: adding petroleum ether (boiling range 30-60° C.) in an amount that is 0.5 times the weight of the remaining emulsified sauce layer and aqueous phase layer from the second extraction, stirring at 500 rpm for 3 minutes to mix and disperse uniformly, and letting it stand for 10 minutes to form three distinct layers from top to bottom: a petroleum ether oil phase, an emulsified sauce layer, and an aqueous phase. Using a pipette to extract the upper petroleum ether oil phase. Combining the petroleum ether oil phases obtained from the first, second, and third extractions to obtain a petroleum ether oil mixture;

(3) Filtering the petroleum ether oil mixture obtained in step (2) through an anhydrous sodium sulfate funnel (with anhydrous sodium sulfate in an amount equal to 15% of the theoretical mass of oil in the sauce), collecting it into a recovery bottle of constant weight (115.36 g), then rinsing the filter paper and funnel with 15 mL of blank petroleum ether, and collecting the dehydrated petroleum ether oil mixture;

(4) Performing rotary evaporation on the dehydrated petroleum ether oil mixture obtained in step (3) at a temperature of 40° C. and a vacuum degree of −0.08 MPa, using a condenser at −15° C. to recover the petroleum ether until no petroleum ether drips from the condenser and the oil has no petroleum ether odor. Continue rotary evaporation for an additional 10 minutes to further reduce solvent residue, obtaining the oil in the recovery bottle;

(5) Wiping the surface of the recovery bottle multiple times (first using dry gauze to remove moisture from the surface of the recovery bottle, then using gauze soaked in anhydrous ethanol to wipe the surface, and finally using dry gauze to remove any residual ethanol from the surface of the recovery bottle). Blowing with nitrogen gas at a pressure of 0.1 MPa for 15 minutes to further reduce solvent residue in the oil, and reducing the oil to room temperature under nitrogen protection to minimize the effects of high-temperature oxidation. After cooling, weighing the recovery bottle containing the oil, which is 144.12 g;

(6) Testing the fat content, peroxide value, and acid value of the oil after nitrogen blowing in step (5). The fat content is tested as follows:

fat content=(144.12−115.36)/100.18×100%=28.71% [oil extraction rate=(144.12−115.36)/(100.18× 0.3)×100%=95.70%], the oil is transparent light yellow;

the peroxide value is tested to be 0.071 g/100 g, according to the method specified in GB 5009.227-2016;

the acid value is tested to be 0.76 mg/g, according to the method specified in GB 5009.229-2016.

Comparative Example 1

(1) Adding petroleum ether (boiling range 30-60° C.) in an amount that is 2.5 times the weight of the 80.23 g of salad dressing (with a theoretical oil content of 40% by weight) to the salad dressing, stirring at 1000 rpm for 3 minutes to mix and disperse uniformly, and letting it stand for 15 minutes to form two distinct layers from top to bottom: a petroleum ether oil phase and a salad dressing aqueous phase. Using a pipette to extract the upper petroleum ether oil phase, leaving the salad dressing aqueous phase;

second extraction: adding petroleum ether (boiling range 30-60° C.) in an amount that is equal to the weight of the remaining salad dressing aqueous phase from the first extraction, stirring at 500 rpm for 3 minutes to mix and disperse uniformly, and letting it stand for 5 minutes to form two distinct layers from top to bottom: a petroleum ether oil phase and a salad dressing aqueous phase. Using a pipette to extract the upper petroleum ether oil phase, leaving the salad dressing aqueous phase;

third extraction: adding petroleum ether (boiling range 30-60° C.) in an amount that is equal to the weight of the remaining salad dressing aqueous phase from the second extraction, stirring at 500 rpm for 3 minutes to mix and disperse uniformly, and letting it stand for 5 minutes to form two layers from top to bottom: a petroleum ether oil phase and a salad dressing aqueous phase. Using a pipette to extract the upper petroleum ether oil phase. Combining the petroleum ether oil phases obtained from the first, second, and third extractions to obtain a petroleum ether oil mixture;

(2) Filtering the petroleum ether oil mixture obtained in step (1) through an anhydrous sodium sulfate funnel (with anhydrous sodium sulfate in an amount equal to 15% of the theoretical mass of oil in the sauce), collecting it into a recovery bottle of constant weight, then rinsing the filter paper and funnel with 15 mL of blank petroleum ether, and collecting the dehydrated petroleum ether oil mixture;

(3) Performing rotary evaporation on the dehydrated petroleum ether oil mixture obtained in step (2) at a temperature of 35° C. and a vacuum degree of −0.09 MPa, using a condenser at −12° C. to recover the petroleum ether until no petroleum ether drips from the condenser and the oil has no petroleum ether odor. Continue rotary evaporation for an additional 8 minutes to further reduce solvent residue. However, almost no oil is obtained in the recovery bottle, making it insufficient for subsequent fat content, peroxide value, and acid value tests.

Comparative Example 2

According to the acid hydrolysis method specified in GB 5009.6-2016.

Remove the test tube and weigh 10.35 g of composite sauce (with a theoretical oil content of 30% by weight). Add 10 mL of ethanol and mix. After cooling, transfer the mixture to a 100 mL stoppered graduated cylinder. Rinse the test tube several times with 25 mL of anhydrous ether and pour the rinses into the graduated cylinder. Once all the anhydrous ether is added to the graduated cylinder, stopper it and shake for 1 minute. Carefully unstopper to release the gas, restopper, and let it stand for 12 minutes. Carefully unstopper again and rinse the stopper and the mouth of the graduated cylinder with ether to remove any adhering fat. Let it stand for 10 to 20 minutes until the upper liquid is clear. Withdraw the supernatant into a pre-weighed conical flask. Add 5 mL of anhydrous ether to the graduated cylinder, shake, let it stand, and again withdraw the upper ether layer into the receiving flask (118.25 g).

Remove the receiving flask and recover the anhydrous ether or petroleum ether. When the solvent remaining in the receiving flask is 1 to 2 mL, evaporate it to dryness in a water bath. Then dry at 100° C.±5° C. for 1 hour, cool in a desiccator for 0.5 hours, and weigh (121.24 g).

fat content=(121.24−118.25)/10.35×100%=28.89%
[oil extraction rate=(121.24−118.25)/(10.35× 0.3)×100%=96.45%], the oil is transparent and slightly light dark brown;

the peroxide value is tested to be 0.11 g/100 g, according to the method specified in GB 5009.227-2016;

the acid value is tested to be 3.21 mg/g, according to the method specified in GB 5009.229-2016.

Comparative Example 3

According to the alkali hydrolysis method specified in GB 5009.6-2016:

Weigh 10.64 g of composite sauce (with a theoretical oil content of 30% by weight) into an extraction bottle, add 2.0 mL of ammonia solution, mix thoroughly, and immediately place the extraction bottle in a water bath at 65° C.±5° C., heating for 15 to 20 minutes. Occasionally remove and shake. After heating, cool to room temperature and let it stand for 30 seconds.

Extraction step (1): add 10 mL of ethanol and mix gently but thoroughly, avoiding the liquid from reaching the neck of the bottle. If necessary, add 2 drops of Congo red solution. step (2): add 25 mL of ether, stopper the bottle, and position the extraction bottle horizontally on a shaker, ensuring the small bulb extension is pointing upwards and clamped securely. Shake at about 100 times per minute for 1 minute. Manual shaking is also acceptable, but care must be taken to avoid forming a persistent emulsion. After cooling the extraction bottle, carefully unstopper it and rinse the stopper and neck with a small amount of the mixed solvent, allowing the rinse to flow into the extraction bottle. Step (3): add 25 mL of petroleum ether, stopper with the re-wetted stopper, and shake gently for 30 seconds as described in step (2). Step (4): place the stoppered extraction bottle in a centrifuge and centrifuge at 500 to 600 rpm for 5 minutes, or alternatively, let it stand for at least 30 minutes until the upper layer is clear and well-separated from the aqueous phase. Step (5): carefully unstopper the bottle, rinse the stopper and inner neck with a small amount of the mixed solvent, allowing the rinse to flow into the extraction bottle. If the phase interface is below the junction of the small bulb and the bottle body, slowly add water along the edge of the bottle to raise the liquid level above this junction to facilitate decanting. Step (6): decant the upper layer as completely as possible into a pre-weighed fat collection bottle containing boiling stones, avoiding decanting the aqueous layer. Step (7): rinse the outer neck of the extraction bottle with a small amount of mixed solvent, collecting the rinse in the fat collection bottle. Avoid splashing the solvent outside the extraction bottle. Step (8): add 5 mL of ethanol to the extraction bottle, rinse the inner neck with ethanol, and mix as described in step (1). Repeat steps (2) to (7) using 15 mL of anhydrous ether and 15 mL of petroleum ether for the second extraction. Step (9): add 5 mL of ethanol to the extraction bottle, rinse the inner neck with ethanol, and mix as described in step 1. Repeat steps 17.2.2 to 17.2.7 using 15 mL of anhydrous ether and 15 mL of petroleum ether for the second extraction.

Combine all the extraction solutions in the collection bottle (185.73 g), and remove the solvent by distillation. Before distillation, rinse the inner neck with a small amount of mixed solvent. Dry the fat collection bottle in an oven at 100° C.±5° C. for 1 hour, then cool in a desiccator for 0.5 hours before weighing (188.78 g).

fat content=(188.78−185.73)/10.64×100%=28.67% [oil extraction rate=(188.78−185.73)/(10.64×0.3)×100%=95.61%], the oil is transparent with a slight yellow-green tint;

the peroxide value is tested to be 0.13 g/100 g, according to the method specified in GB 5009.227-2016;

the acid value is not detected, according to the method specified in GB 5009.229-2016.

FIG. 1 is a comparison chart showing the color differences of oils extracted by different methods in Example 3, Comparative Example 2, and Comparative Example 3.

The oil extracted in Example 3 using an efficient and gentle method is pale yellow, similar to the color of the oil added to the product formula, and the sensory qualities are not affected by the extraction method. Additionally, the measured acid value and peroxide value are not influenced by the extraction method, providing more scientific and representative results.

Comparative Example 2 uses the acid hydrolysis method for testing. While the oil extraction rate can be ensured, the residues from acid hydrolysis interfere with the peroxide value and acid value tests to varying degrees. The extracted oil is noticeably darker in color; the peroxide value, although within a controllable range, is relatively high, and the acid value is significantly higher, rendering the data unreliable.

Comparative Example 3 uses the alkali hydrolysis method for testing. While the oil extraction rate can be ensured, the residues from alkali hydrolysis interfere with the peroxide value and acid value tests to varying degrees. The extracted oil is darker in color; the peroxide value, although within a controllable range, is relatively high, and the acid value cannot be tested at all.

The above examples represent preferred embodiments of the present invention. However, the implementation of the present invention is not limited to the above examples. Any modifications, adjustments, substitutions, combinations, or simplifications made without departing from the spirit and principles of the present invention should be considered equivalent replacements and are included within the scope of the present invention.

The invention claimed is:

1. A method for extracting oil from a sauce and simultaneously determining fat content, peroxide value, and acid value, comprising the following steps:
   (1) adding water in an amount that is 0.5 to 3 times the weight of the sauce, stirring at 500 to 2000 rpm for 2 to 5 minutes to disperse uniformly and obtain a suspension, wherein the sauce is an oil-rich emulsified encapsulated sauce;
   (2) while stirring at 500 to 1000 rpm, adding edible salt amounting to 2-5% of the mass of the suspension and stirring until completely dissolved;
   (3) adding 95% ethanol (by volume) in an amount that is 1 to 3 times the weight of the sauce in step (1), stirring at 500 to 1000 rpm for 2 to 5 minutes to mix and disperse evenly;
   (4) conducting three extractions sequentially:
   first extraction: adding petroleum ether in an amount that is 1 to 3 times the weight of the sauce in step (1), stirring at 500 to 1000 rpm for 2 to 5 minutes to mix and disperse uniformly, and letting the suspension stand for 10 to 15 minutes to form three distinct layers from top to bottom: a petroleum ether oil phase layer, an emulsified sauce layer, and an aqueous phase layer, using a pipette to extract the upper petroleum ether oil phase layer, leaving the emulsified sauce layer and aqueous phase layer mixture;
   second extraction: adding petroleum ether in an amount that is 1 to 1.5 times the weight of the sauce in step (1) to the emulsified sauce layer and aqueous phase layer remaining from the first extraction, stirring at 300 to 700 rpm for 2 to 5 minutes to mix and disperse uniformly, and letting the suspension stand for 5 to 10 minutes to form three distinct layers from top to bottom: a petroleum ether oil phase layer, an emulsified sauce layer, and an aqueous phase layer, using a pipette to extract the upper petroleum ether oil phase layer, leaving the emulsified sauce layer and aqueous phase layer mixture;
   third extraction: adding petroleum ether in an amount that is 0.5 to 1.0 times the weight of the sauce in step (1) to the emulsified sauce layer and aqueous phase layer remaining from the second extraction, stirring at 300 to 700 rpm for 2 to 5 minutes to mix and disperse uniformly, and letting the suspension stand for 5 to 10 minutes to form three distinct layers from top to bottom: a petroleum ether oil phase layer, an emulsified sauce layer, and an aqueous phase layer, using a pipette to extract the upper petroleum ether oil phase layer, combining the petroleum ether oil phase layers obtained from the first, second, and third extractions to obtain petroleum ether oil mixture;
   (5) filtering the petroleum ether oil mixture obtained in step (4) through an anhydrous sodium sulfate funnel, collecting it into a recovery bottle, then rinsing a filter paper and funnel with 5-20 mL of blank petroleum ether, and obtaining and collecting a dehydrated petroleum ether oil mixture;
   (6) performing rotary evaporation on the dehydrated petroleum ether oil mixture obtained in step (5) at a temperature of 25-40° C. and a vacuum degree of 0.04 to 0.09 MPa, using a condenser at −5 to −20° C. to recover the petroleum ether until no petroleum ether drips from the condenser and the oil has no petroleum ether odor, continuing rotary evaporation for an additional 5-10 minutes to further reduce solvent residue, obtaining the oil in the recovery bottle;
   (7) wiping an outer surface of the recovery bottle multiple times, then blowing with nitrogen gas at a pressure of 0.01-0.2 MPa for 5-30 minutes to further reduce solvent residue in the oil, and reducing the oil to room temperature under nitrogen protection to minimize the oxidation of the oil; and
   (8) testing the fat content, peroxide value, and acid value of the oil after the nitrogen blowing in step (7).

2. The method for extracting oils from the sauce while simultaneously determining fat content, peroxide value, and acid value according to claim 1, wherein, in steps (4) and (5), the petroleum ether used has a boiling range of 30-60° C.

3. The method for extracting oils from the sauce while simultaneously determining fat content, peroxide value, and acid value according to claim 1, wherein, in step (8), the fat content is calculated using the following formulas:

fat content=(mass of the extracted oil in step (6)/mass of the sauce in step (1)×100%.

4. The method for extracting oils from the sauce while simultaneously determining fat content, peroxide value, and acid value according to claim 1, wherein, in step (1), the water added is reverse osmosis (RO) water; and in step (2), the edible salt is non-iodized salt or NaCl.

5. The method for extracting oils from the sauce while simultaneously determining fat content, peroxide value, and acid value according to claim 1, wherein, in step (7), the recovery bottle is wiped multiple times: first, using dry gauze to remove moisture from the outer surface; then, using gauze soaked in anhydrous ethanol to wipe the outer surface; and finally, using dry gauze to remove any residual ethanol from the outer surface.

* * * * *